US009927356B2

(12) United States Patent
Skibo

(10) Patent No.: US 9,927,356 B2
(45) Date of Patent: Mar. 27, 2018

(54) SYSTEMS AND METHODS FOR DETECTING GASES, AIRBORNE COMPOUNDS, AND OTHER PARTICULATES

(71) Applicant: SMS Sensors Incorporated, Monmouth Junction, NJ (US)

(72) Inventor: Richard J. Skibo, Skillman, NJ (US)

(73) Assignee: SMS Sensors Incorporated, Monmouth Junction, NJ (US)

( * ) Notice: Subject to any disclaimer, the term of this patent is extended or adjusted under 35 U.S.C. 154(b) by 0 days.

(21) Appl. No.: 15/074,840

(22) Filed: Mar. 18, 2016

(65) Prior Publication Data
US 2016/0274025 A1    Sep. 22, 2016

Related U.S. Application Data

(60) Provisional application No. 62/136,417, filed on Mar. 20, 2015.

(51) Int. Cl.
*G01N 21/39* (2006.01)
*G01S 17/88* (2006.01)
(Continued)

(52) U.S. Cl.
CPC ............ *G01N 21/39* (2013.01); *G01N 21/31* (2013.01); *G01N 21/3504* (2013.01);
(Continued)

(58) Field of Classification Search
CPC .... G01N 21/3504; G01N 21/39; G01N 21/31; G01N 21/35; G01N 21/59; G01N 21/61;
(Continued)

(56) References Cited

U.S. PATENT DOCUMENTS

| 3,766,380 A * | 10/1973 | Menzies | G01N 21/39 |
|---|---|---|---|
| | | | 250/338.5 |
| 4,426,640 A * | 1/1984 | Becconsall | G01S 17/95 |
| | | | 250/338.5 |

(Continued)

FOREIGN PATENT DOCUMENTS

CN    103838210 A    6/2014

OTHER PUBLICATIONS

International Search Report of the International Searching Authority dated Jun. 20, 2016, issued in connection with International Application No. PCT/US16/23269 (3 pages).

(Continued)

*Primary Examiner* — Gordon J Stock, Jr.
(74) *Attorney, Agent, or Firm* — McCarter & English, LLP

(57) ABSTRACT

Systems and methods for detecting gases, airborne compounds, and other particulates, are provided. The system detects materials of interest, including but not limited to, volatile organic compounds, aerosols, particulates, and biological and other pathogens in a three dimensional volume over an area of interest. The system detects the concentration of analytes of interest in the presence of atmospheric contaminants. Data points form a three-dimensional "point cloud" to which particle swarm optimization and feature extraction algorithms are applied, providing leak detection, mapping of chemical plumes, and short-term and long-term flux measurements, among other functions.

30 Claims, 13 Drawing Sheets

(51) Int. Cl.

| | | |
|---|---|---|
| *G01N 21/31* | (2006.01) | |
| *G01N 21/3504* | (2014.01) | |
| *G01S 17/95* | (2006.01) | |
| *G01S 7/48* | (2006.01) | |
| *G01N 21/53* | (2006.01) | |
| *G01N 21/17* | (2006.01) | |
| *G01N 21/47* | (2006.01) | |
| *G06N 99/00* | (2010.01) | |

(52) U.S. Cl.
CPC ......... *G01N 21/538* (2013.01); *G01S 7/4802* (2013.01); *G01S 17/88* (2013.01); *G01S 17/95* (2013.01); *G06N 99/005* (2013.01); *G01N 2021/1793* (2013.01); *G01N 2021/1795* (2013.01); *G01N 2021/394* (2013.01); *G01N 2021/399* (2013.01); *G01N 2021/4709* (2013.01); *G01N 2201/10* (2013.01)

(58) Field of Classification Search
CPC .......... G01N 21/3509; G01N 21/3518; G01N 2021/394; G01N 2021/1793; G01N 2021/1797; G01N 2021/4709; G01N 2021/1704; G01N 2021/3133; G01N 2021/3185; G01N 2021/3595; G01N 2021/3513; G01N 2021/3522; G01N 2021/3527; G01N 2021/3545; G01N 2021/355; G01N 2021/1795; G01N 33/0047; G01N 33/0036; G01N 33/0057; G01N 2021/3129; G01J 2003/423; G01J 2003/4332; G01J 2003/4334; G01J 2003/4338; G01J 3/4338; G01J 3/42; G01J 3/425; G01J 3/427; G01J 3/433; G01S 7/483; G01S 7/484; G01S 7/486; G01S 7/4861; G01S 7/4863; G01S 17/02; G01S 17/026; G01S 17/102; G01S 17/107; G01S 17/88; G01S 17/89
See application file for complete search history.

(56) References Cited

U.S. PATENT DOCUMENTS

| | | | | |
|---|---|---|---|---|
| 5,157,257 | A * | 10/1992 | Geiger | G01N 21/3504 250/338.5 |
| 5,250,810 | A * | 10/1993 | Geiger | G01N 21/3504 250/338.5 |
| 5,614,715 | A * | 3/1997 | Jones | H04N 3/09 250/332 |
| 6,664,533 | B1 * | 12/2003 | van der Laan | G01J 3/433 250/222.2 |
| 6,822,742 | B1 * | 11/2004 | Kalayeh | G01N 21/31 250/338.1 |
| 7,342,228 | B1 * | 3/2008 | O'Connell | G01N 21/3504 250/339.06 |
| 7,453,552 | B1 | 11/2008 | Miesak | |
| 8,078,410 | B2 * | 12/2011 | Marquardt | G01N 21/21 356/364 |
| 8,541,744 | B1 * | 9/2013 | Liu | G01S 17/42 250/338.5 |
| 9,366,872 | B2 * | 6/2016 | Honea | G02B 27/0927 |
| 2006/0011840 | A1 * | 1/2006 | Bryce | G01N 21/314 250/338.5 |
| 2006/0012797 | A1 * | 1/2006 | Chang | G01J 3/02 356/484 |
| 2006/0268947 | A1 * | 11/2006 | Kalayeh | G01N 21/3504 372/20 |
| 2007/0024840 | A1 | 2/2007 | Fetzer et al. | |
| 2007/0045542 | A1 * | 3/2007 | Hashmonay | G01N 21/3504 250/339.12 |
| 2007/0291994 | A1 | 12/2007 | Kelle et al. | |
| 2008/0225273 | A1 | 9/2008 | Ershov et al. | |
| 2010/0006760 | A1 | 1/2010 | Lee et al. | |
| 2010/0130371 | A1 | 5/2010 | Collette et al. | |
| 2011/0116074 | A1 | 5/2011 | Valla et al. | |
| 2013/0100451 | A1 * | 4/2013 | Hager | G01N 21/532 356/438 |
| 2013/0128042 | A1 * | 5/2013 | Bridge | H04N 5/232 348/143 |
| 2014/0160479 | A1 * | 6/2014 | Hager | G01N 21/3504 356/438 |
| 2015/0036135 | A1 | 2/2015 | Knopp et al. | |

OTHER PUBLICATIONS

Written Opinion of the International Searching Authority dated Jun. 20, 2016, issued in connection with International Application No. PCT/US16/23269 (10 pages).

* cited by examiner

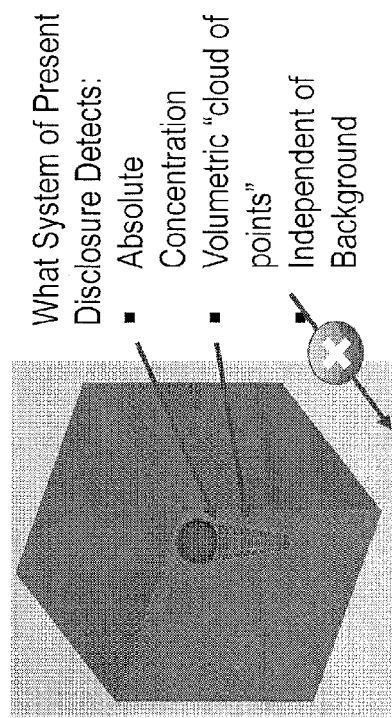

FIG. 10C

What System of Present Disclosure Detects:
- Absolute Concentration
- Volumetric "cloud of points"
- Independent of Background

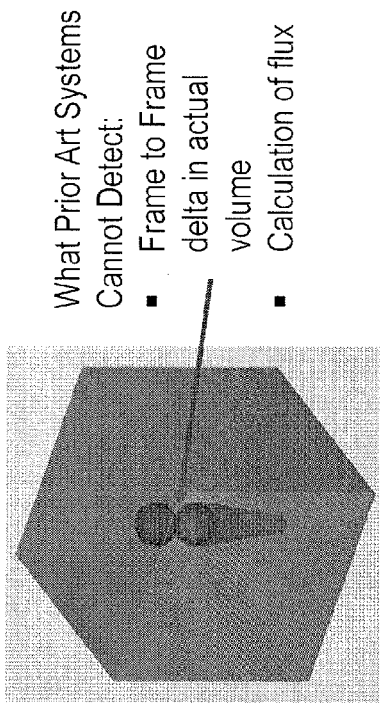

FIG. 10D

What Prior Art Systems Cannot Detect:
- Frame to Frame delta in actual volume
- Calculation of flux

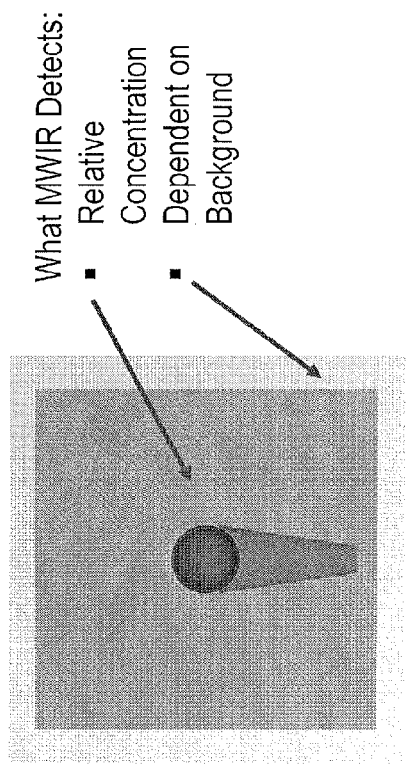

FIG. 10A

What MWIR Detects:
- Relative Concentration
- Dependent on Background

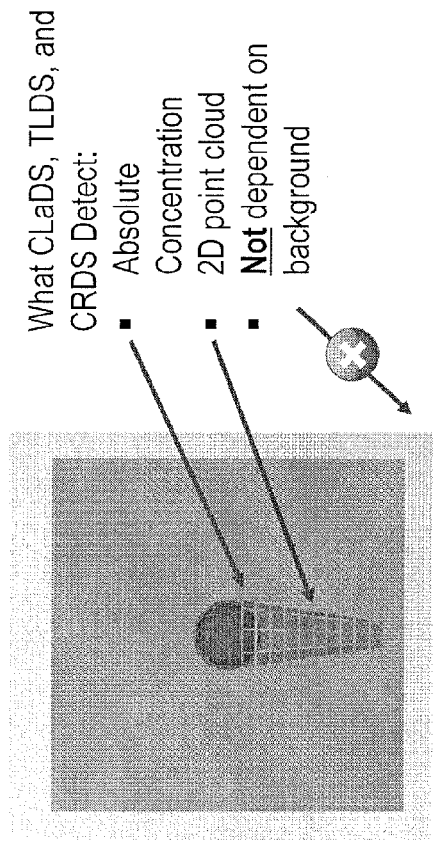

FIG. 10B

What CLaDS, TLDS, and CRDS Detect:
- Absolute Concentration
- 2D point cloud
- Not dependent on background

SYSTEMS AND METHODS FOR DETECTING GASES, AIRBORNE COMPOUNDS, AND OTHER PARTICULATES

RELATED APPLICATIONS

This application claims the benefit of U.S. Provisional Application Ser. No. 62/136,417 filed Mar. 20, 2015, the entire disclosure of which is expressly incorporated herein by reference.

BACKGROUND OF THE INVENTION

Field of the Invention

The present disclosure relates to large-aperture, 3-dimensional spectroscopic LIDAR systems and methods. More specifically, the present disclosure relates to a standoff detection system that can detect areas of airborne material in a 3-dimensional envelope in parts per million (ppm) or lower concentration in the atmosphere.

Related Art

The accurate, real-time measurement of airborne materials, gases, and related aerosol or particulate compounds over a broad area is a persistent challenge in the monitoring of atmospheric and other environments. For example, the measurement of explosive and/or toxic gases can be vitally important for the safety of workers working in environments where such gases are commonly found, and even for the general population near or downwind of such environments. Ideally, measurements could be made in a non-contact, remote, or "standoff" mode and overall be rapid, cost effective, safe, and independent of atmospheric baseline concentrations of the analytes of interest, frequent calibration, or excessive human intervention. In addition to the concentration of the airborne contaminate, another important parameter is the determination of the flux of the contaminant over time, e.g., change in mass volume in a specific volume or specific discharge times of the concentration.

Standoff detection of volatile organic compounds is accomplished in the prior art by a wide range of technologies, including TDLAS (Tunable Diode Laser Spectroscopy), DIAL (Differential Absorption Lidar), FTIR (Fourier Transform Infrared) spectroscopy, and CM-CLADS (Chirped Mode Laser Dispersion Spectroscopy). However, none of these technologies are capable of providing a three dimensional (3D) profile of the atmospheric concentration of airborne compounds in the volumetric space above an area of interest. For example, none of the methods discussed above support a long-distance 3D mapping system for gas emissions and the requisite plume analysis and the resulting flux calculations, or even persistent standoff monitoring in a cost-effective manner. Further, none of these systems support long-term, self-calibrating, zero baseline, and path-independent features which are mandatory for unattended operation.

FIG. 1A is a topological view of a ground-based sensor network (e.g., a "ground truth" baseline method) of the prior art for measuring concentrations of volatile organic compounds (VOCs), in this case, benzene with a network of ground-based wireless sensors 2 placed in a 300 acre tank farm. The sensors 2 acquire data at 1 to 10 minute intervals and transmit analytical information along with meteorological information to a remote network site. FIG. 1B is a typical time-sequenced history of the benzene concentration at a particular sensor node 2 of the system shown in FIG. 1A. FIG. 1C illustrates a "time slice" of the measurement of FIG. 1B with superimposed meteorological information (e.g., wind velocities). The actual concentration of benzene and the corresponding time-resolved flux is computed and predicted from the point measurements, dispersion coefficients, and the factoring in of the effects of selected meteorological and topological features.

FIG. 2 is spectral diagram of numerous areas where a VOC such as benzene, for example, can be detected by the difference in absorption between benzene's normal isotope $CH_4$ and atmospheric gases. A cluster of spectral bands around 3.41 and 5-6.7μ are shown.

FIGS. 3A and 3B illustrate a Differential Absorption Lidar (DIAL) detection and imaging system for mapping benzene clouds and plumes in the atmosphere. The system shown in FIG. 3A is used for persistent mapping of an area around a site of interest. FIG. 3B is a diagram depicting the various concentrations of benzene plumes in the atmosphere over a leaking gas production facility. The intensity of the clouds determines the relative concentration of the benzene, but is strongly dependent on atmospheric conditions including water vapor lines and the overall emissivity of the background.

FIGS. 4A-C are diagrams illustrating the state of the art capabilities for long-distance detection of an important greenhouse gas, methane, using mid-wavelength infrared (MWIR) hyperspectral imaging. MWIR hyperspectral imaging can detect methane clouds via absorption lines post event, but plume tracking is difficult. FIG. 4A is a diagram illustrating a 3.3μ absorption band 72 of the antisymetrical valence oscillation "vibrational" and a 7.7μ absorption band 74 of the deformation oscillation. FIG. 4B is a diagram illustrating that the 3.3μ absorption line 76 is close to the peak spectral response of the broadband MWIR camera. FIG. 4C illustrates a wide field of view image over a leaking gas platform.

The development of data using an ensemble of conventional techniques, as depicted in FIGS. 1A-3B, is limited by the distributed and episodic nature of fugitive benzene and other VOC emissions. Standard methodologies described above, as well as the accompanying atmospheric dispersion modeling and related mathematical simulations, are derived from point sampling methods that are predicated on well-mixed aerosols and gases. However, such models are severely compromised by disrupted wind flow fields, varied surface temperatures, and topologies of related manmade and natural structures.

Accordingly, what is needed are systems and methods for persistent surveillance of gases, volatile organic compounds, and airborne dispersed compounds that overcome the aforementioned deficiencies of the prior art.

SUMMARY OF THE INVENTION

The present disclosure relates to systems and methods for detecting gases, airborne compounds, and other particulates. In particular, the system detects materials of interest, including but not limited, to volatile organic compounds, aerosols, particulates, biological, and other pathogens in a three-dimensional (3D) volume over an area of interest. The system can detect the concentration of analytes of interest in the presence of atmospheric contaminants. In addition, the detection and localization of the concentration data points are used to construct a 3D "point cloud" which permits the use of data analysis algorithms (e.g., particle swarm optimization) coupled with feature extraction algorithms (e.g., support vector machines). The comprehensive data set generated by the system permits the implementation of various functions such as leak detection, mapping of chemical plumes, short-term and long-term flux measurement, and detection of combustible or toxic gases, among other functions. Overall, the present disclosure provides an economical means for persistent surveillance of areas of interest in an unattended, standoff manner.

BRIEF DESCRIPTION OF THE DRAWINGS

The foregoing features of the disclosure will be apparent from the following Detailed Description of the Invention, taken in connection with the accompanying drawings, in which:

FIGS. 10A-D are diagrams illustrating advantageous features of the scanning system of the present disclosure;

DETAILED DESCRIPTION OF THE INVENTION

The present disclosure relates systems and methods for detecting gases, airborne compounds, and other particulates, as discussed in detail below in connection with FIGS. 5-11. As used herein, "standoff" detection refers to detection from a distance to permit operation in a remote and/or unattended fashion. The present disclosure, with suitable templates and feature extraction systems, can be employed for the detection of any atmospheric borne materials such as volatile organic compounds, biologicals, chemicals, bacteria, gases, aerosols, particulates, and even bacteria and related compounds. The system can provide a time sequenced concentration map in 3D to permit highly accurate calculation of flux and migration of the compounds of interest. The system also employs an extensive data reduction and analysis subsystem to permit extraction of features in a time resolved manner heretofore not presented in the art. The disclosed systems and methods can be used for many purposes, including detection of explosive gases, harmful gases, and weapons, including those discharging chemical and/or biological agents. The present disclosure has applications in any situation where detection of airborne materials would be desired, such as military situations, terrorism situations, in the mining industry, and in boating to name a few. The disclosed systems and methods could also be employed to detect airborne volcanic ash and its precursors as an adjunct to the international program, Support to Aviation for Volcanic Ash Avoidance (SAVAA).

Figure 1A:
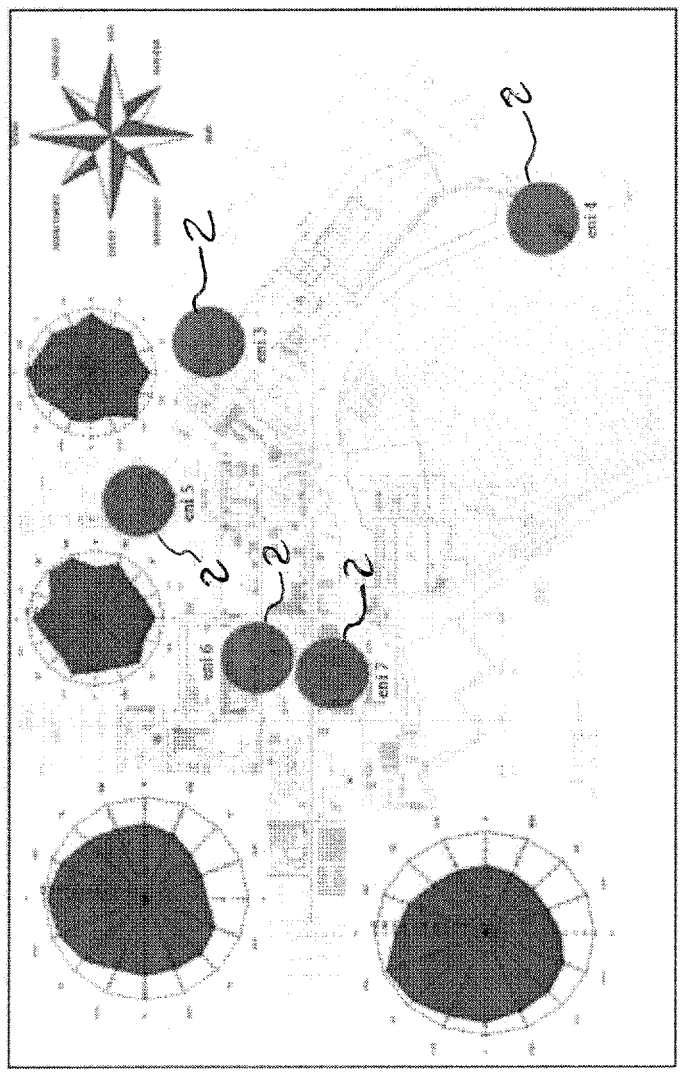
FIG. 1A is a topological view of a ground-based sensor network of the prior art.
Figure 1B:
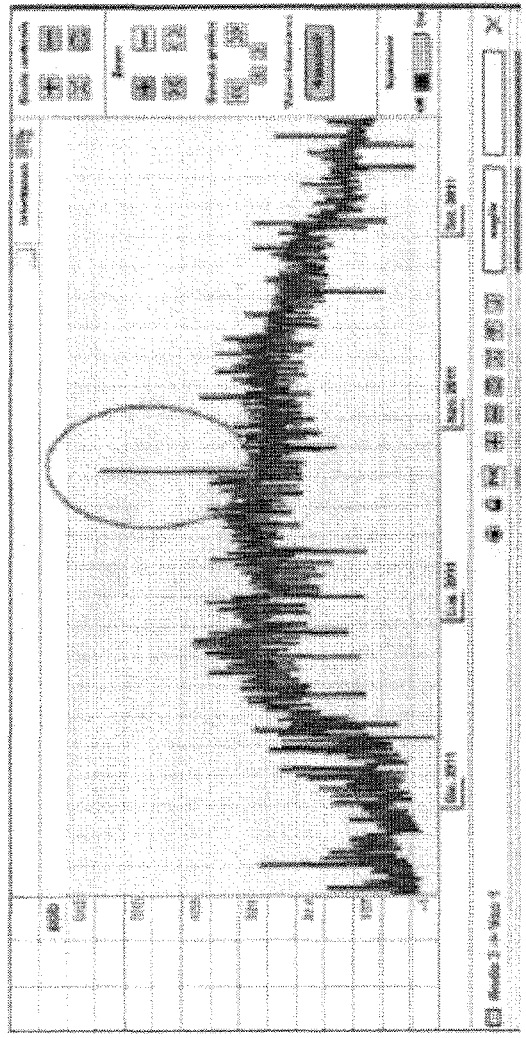
FIG. 1B is a time sequenced history diagram at a sensor node of the sensor network of FIG. 1A.
Figure 1C:
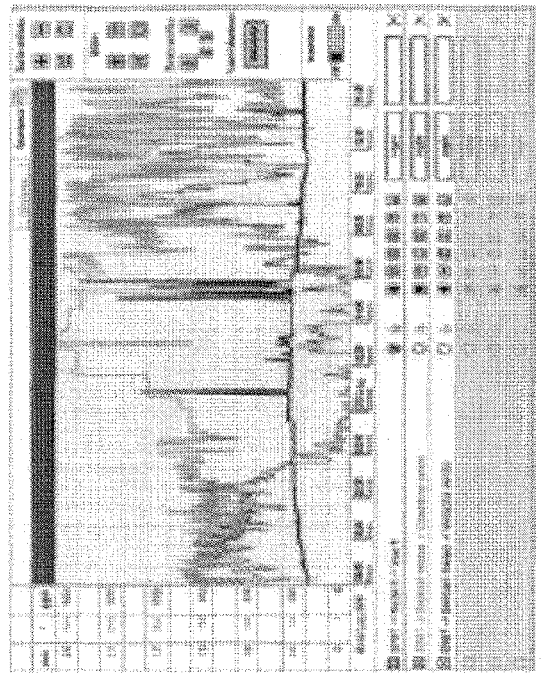
FIG. 1C is a time sequenced history diagram at a sensor node of the sensor network of FIG. 1A with superimposed meteorological information.
Figure 2:
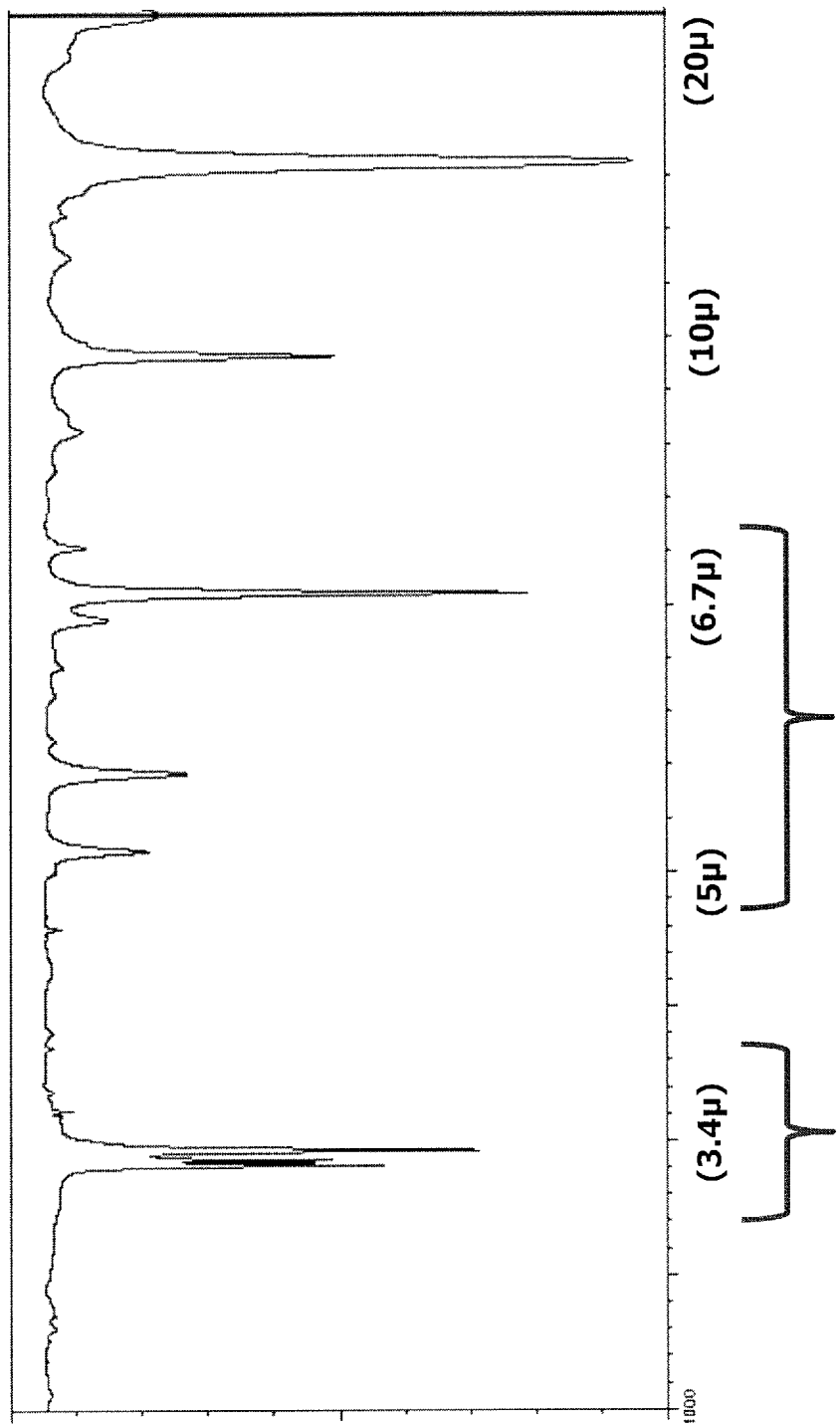
FIG. 2 is a diagram illustrating spectral bands where systems of the prior art can detect volatile organic compounds.
Figure 3B:
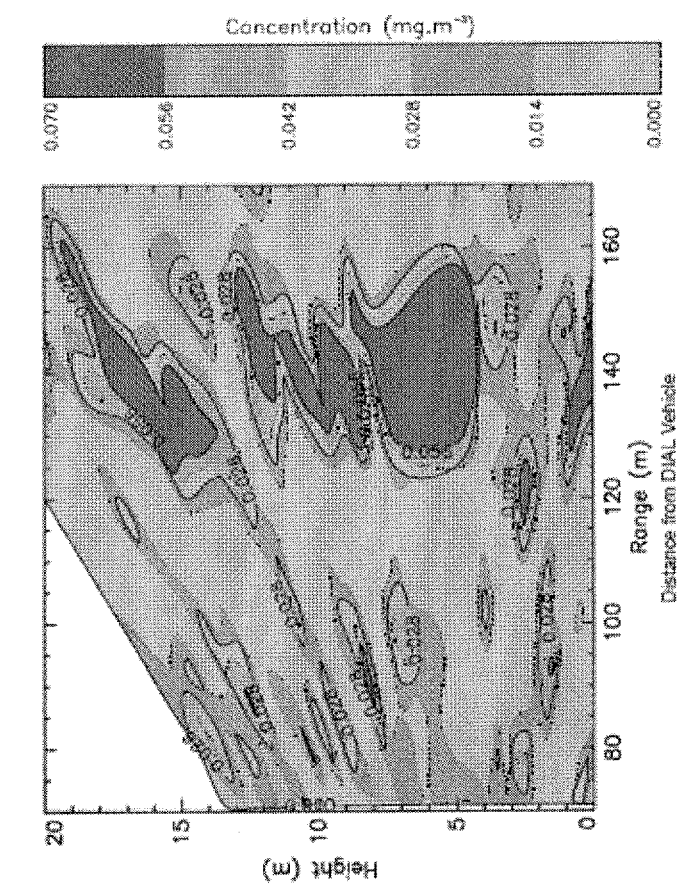
FIG. 3B is a diagram illustrating concentrations of benzene clouds in the atmosphere.
Figure 3A:
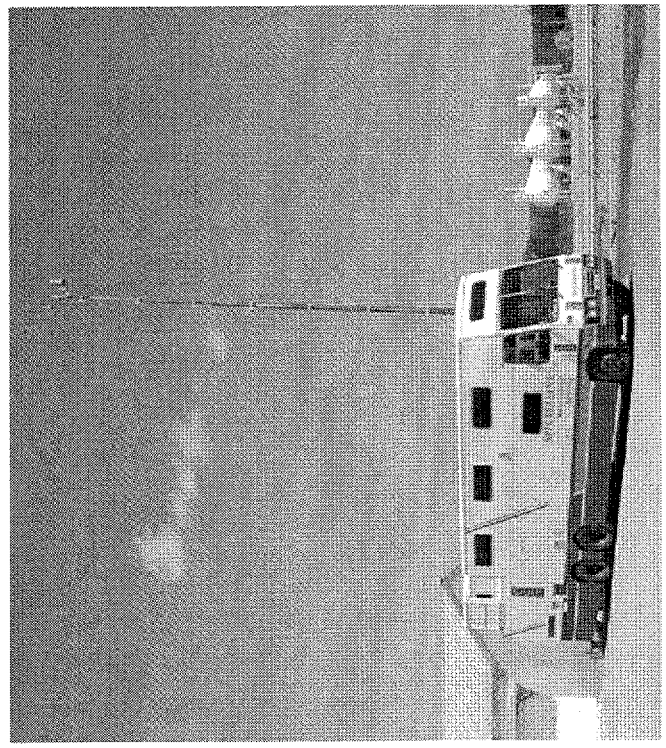
FIG. 3A illustrates a Differential Absorption Lidar (DIAL) system of the prior art for mapping benzene clouds.
Figure 4A:
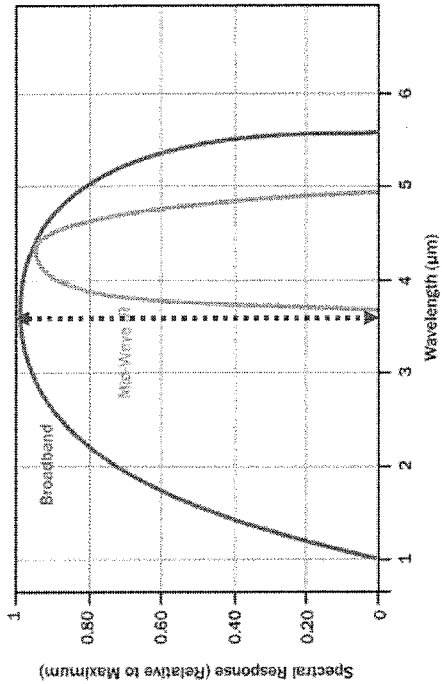
FIGS. 4A-C are diagrams illustrating prior art methods for long distance detection of methane using mid-wavelength infrared (MWIR) hyperspectral imaging.
Figure 4B:
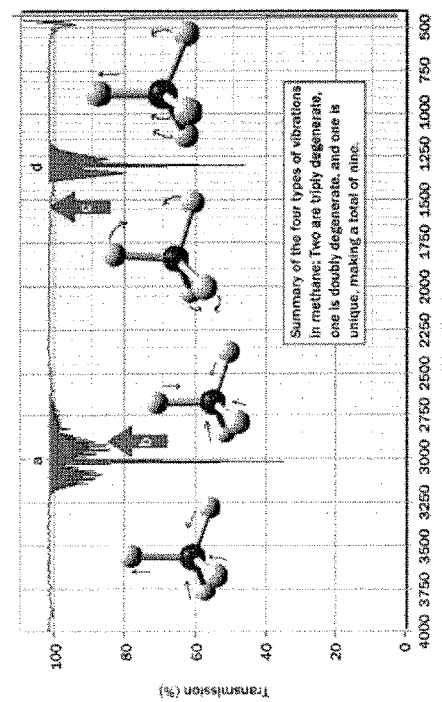
Figure 4C:
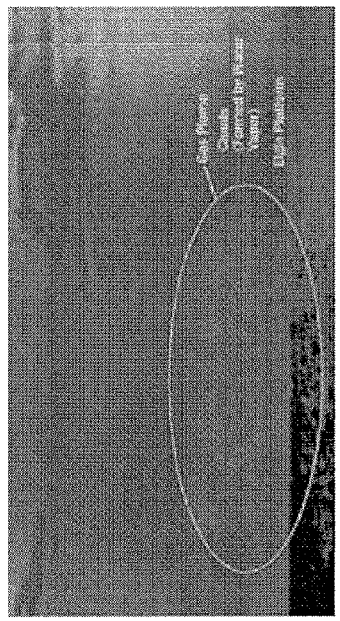
Figure 5:
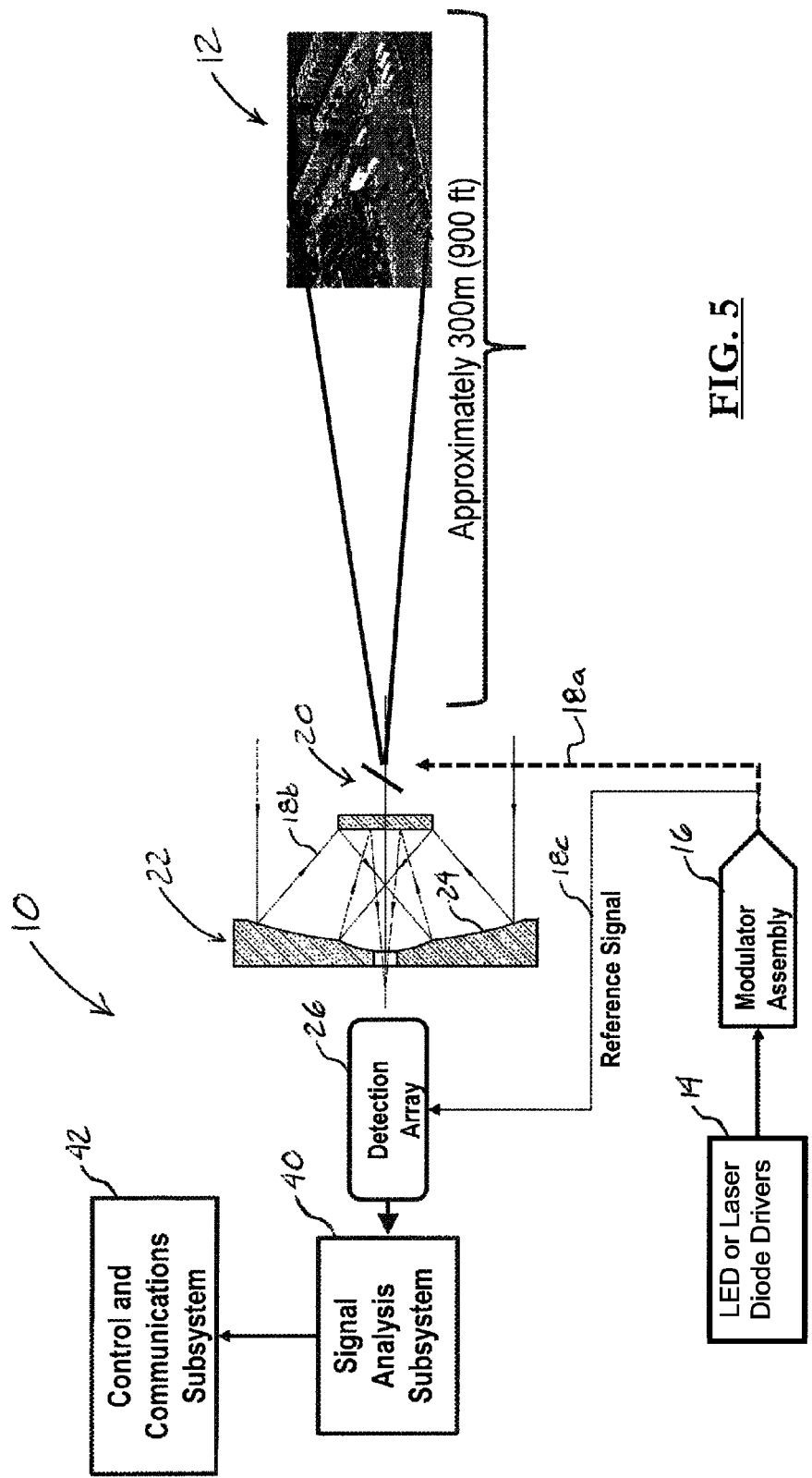
FIG. 5 is a diagram illustrating the scanning system of the present disclosure.

FIG. 5 illustrates a scanning system of the present disclosure, indicated generally at 10, for detecting airborne gases and particulates, such as benzene analytes, in and around a facility 12. The facility 12 could be a gas production facility, or any other suitable location. The system 10 could include an LED or laser diode driver assembly 14, a modulator assembly 16, a scanning array 20, an optical observation device 22, a detection array 26, a signal analysis subsystem 40, and a control and communications subsystem 42. A typical production site 12 with an approximate area of 200 meters (m)×200 m is also shown in FIG. 5. The scanning system 10 could be located approximately 300 m from the production site/site of interest 12, but of course, other distances are acceptable.

The LED or laser diode driver assembly 14 could include one or more LED or laser diodes and drivers which emit light at a group of wavelengths corresponding to areas of interest in the absorption spectrum of the analyte(s) of interest. For example, the wavelengths corresponding to areas of interest for benzene are, approximately, in the 3µ-7µ band. The modulator assembly 16 conditions the LED or laser outputs from the driver assembly 14 and modulates the LED or laser outputs with suitable gating functions to facilitate ranging and time of flight calculations. As shown in FIG. 5, composite laser beams 18a impinge on a scanning array 20 which could include technologies such as galvanometers or digital micromirror assemblies to effect scanning of the remote area of interest. The optical observation device 22, e.g., a large aperture compact compound telescope such as a Gregorian, Cassegrainian, or a hybrid thereof for the collection of the returned backscatter radiation signals 18b from the areas of interest 12. Reflective surfaces 24 of the optical observation device 22 could be enhanced by one or more wavelength-specific metamaterial structures to improve the collection and reflection efficiency of the respective components.

The detection array 26 includes a detector 38 (see FIG. 8) (e.g., an avalanche photodiode (APD) or an array of APD devices), which permits detection of the returned signals 18b, acoustical optical shifters, and circulators which mix the incoming returned signals 18b with a small portion of the transmitted frequency provided as a reference signal 18c.

Figure 8:
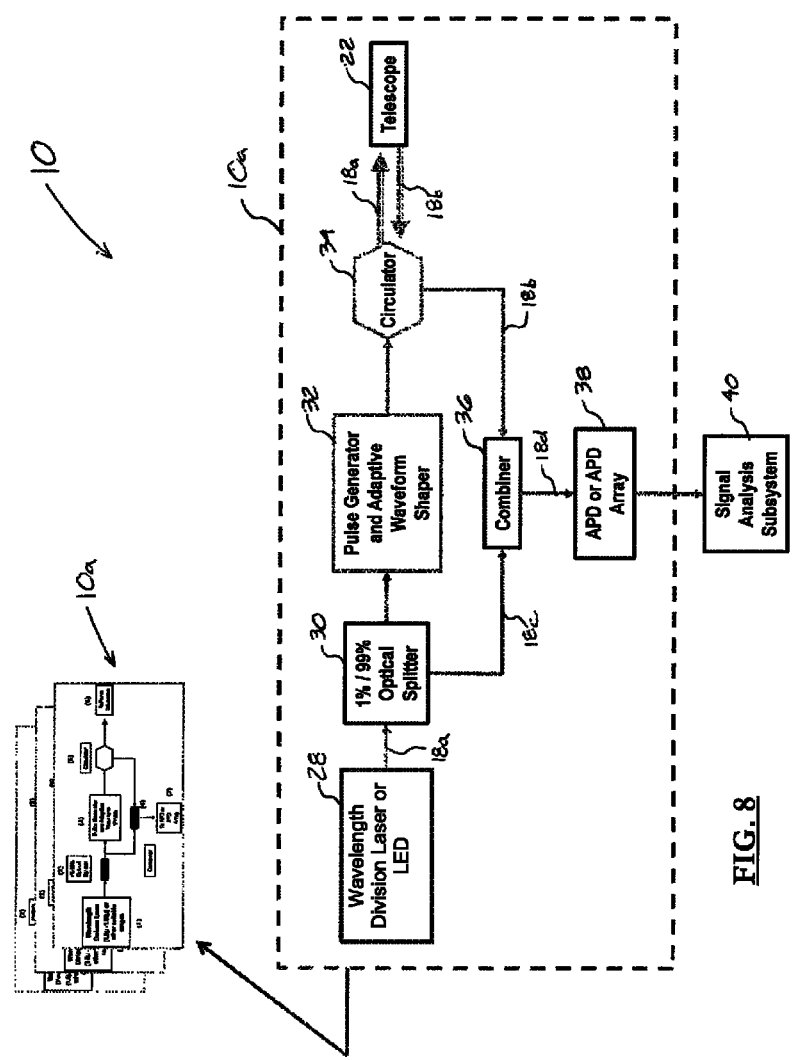
FIG. 8 is a diagram illustrating components of the system of FIG. 5 in greater detail.

Referring now to FIG. 8, the system 10 could include one or more discrete arrays of wavelength subsystems 10a that span the area of interest for the specific analytes. The subsystems 10a could include low cost structures and imprinted waveguide, circulator, and combiner assemblies derived from the telcom industry, the internals of each subsystem 10a including a specific, narrowly-tunable LED or laser 28 feeding a range-gated pulse shaper 32 through an optical splitter 30. The LED or laser 28 could be a wavelength division laser (1.5µ-1.65µ or other suitable ranges). The main output 18a of the LED or laser 28 passes through a circulator 34. An external port of the circulator 34 feeds the telescope 22 and scanning assembly 20 shown in FIG. 5. The range-gated pulse shaper 32 performs two primary functions. The first function is to gate the laser 18a into specific pulse widths which permit the return signal 18b to enter the circulator 34 unobstructed by the outgoing pulse 18a. The second function of the range-gated pulse shaper 32 is to optically shape the pulse, to provide "precompensation" for the dispersion effects of the atmosphere, to ensure that a flat-topped pulse, rather than a corrupted pulse, is presented to the targets. The return pulse 18b from the telescope 22 enters the circulator 34 and is heterodyned against the laser signal 18c by the combiner 36 to detect phase, amplitude, and frequency shifts. The reference signal 18c is provided by a 1% nominal tap from the optical splitter 30, as shown in FIG. 8. The combiner 36 then feeds the combined signal 18d to an Avalanche Photo Diode (APD) 38 of the detector array 26 with a suitable frequency response to match the laser array (e.g., 1.5-3μ with a bandwidth of about 1 GHz and above to permit rapid pulse repetition rates for high resolution and frame rates). The APD receives photons contained in the combined signal 18d and converts the photons to electrical impulses that provide a highly accurate indicator of the intensity and timing of the signal that was backscattered by the area of interest 12. The intensity and timing indicators are provided as raw data which is used by the signal analysis subsystem 40 (discussed hereinbelow) to calculate time-of-flight measurements of backscattered signals from the airborne clouds of analytes.

Time sequencing is performed in conjunction with the detection of the returned signal 18b (combined with reference signal 18c) as detected by the APD or APD array 38 via a high resolution timing circuit (not shown) incorporated in the APD control circuitry. Each feature detected is stored as a data element along with a time value referenced to the incident pulse impinging on the target. A history of responses is gathered so that a correlation between pulses may be effected and profiles of occluded targets can be constructed. To further increase resolution, every pulse could be coded with a specific code so that a correlation between emitted pulses and received pulses could be performed more precisely (e.g., having a greater amount of data points to correlate) to construct the 3-dimensional "point cloud" of the area of interest. The raw, time sequenced, data from the APD 38 is then transmitted to the signal analysis subsystem 40.

In another embodiment, the system 10 of the present disclosure includes "Time-of-Flight" light-emitting diode (LED) scanning functions as an alternative to laser excitation and scanning. For example, the system 10 could include a wide-band or supercontinuum light-emitting diode source providing broadband excitation of an area of interest. The system 10 could also include highly selective narrowband optical filters to provide the equivalent of spectral lines from multiple discrete laser assemblies, responses scanning areas of interest in the spectra of the analytes. Although LED scanning functions provide lower resolution and a smaller field of view (as compared with embodiments utilizing laser assemblies), component costs of LED systems can be orders of magnitude lower and provide systems with form factors suitable for handheld use and investigation.

Referring back to FIG. 5, the signal analysis subsystem 40 performs a group of inter-related functions to analyze the combined signal 18d (see FIG. 8) detected by the APD or APD array 38. The signal analysis subsystem 40 could include the following components:

Spectroscopic Analysis Software;
Ranging Software (for detection of distance);
Doppler Software (required for standoff detection of flow velocity);
Signal Processing, Analog-to-Digital (A/D) conversion, Digital Signal Processing (DSP), and Range Gating Components;
Display and Calibration;
Mathematical Co-Processing Units;
Local Data Storage (for historical data and fuzzy logic learning);
Long Baseline Anomalous Signal Detection; and
Range Gating System (for 3D distance functionality).

As shown in FIG. 5, the system 10 could further include control and communications subsystem 42 which could provide additional data storage, communications to remote monitoring stations, and if required for large facilities, synchronization with other subsystems located at perimeters of the site 12.

Figure 6E:
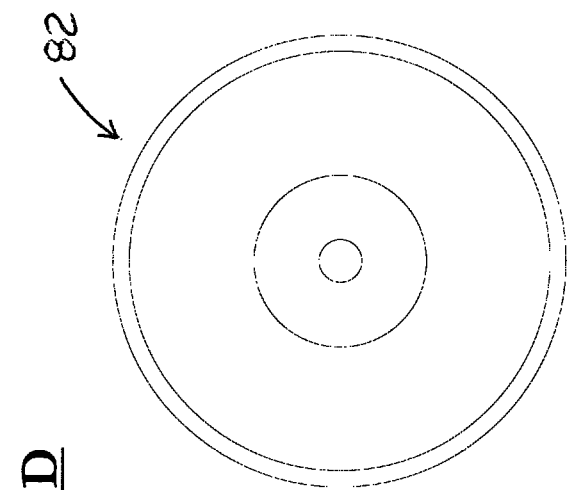
FIGS. 6A-E are diagrams illustrating a main mirror of the scanning system of FIG. 5 in greater detail.
Figure 6D:
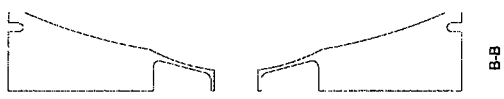
Figure 6C:
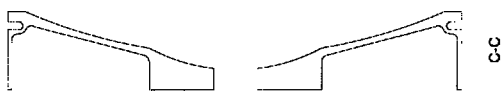
Figure 6B:
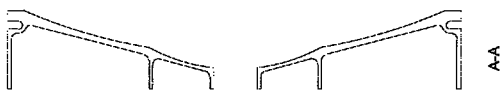
Figure 6A:
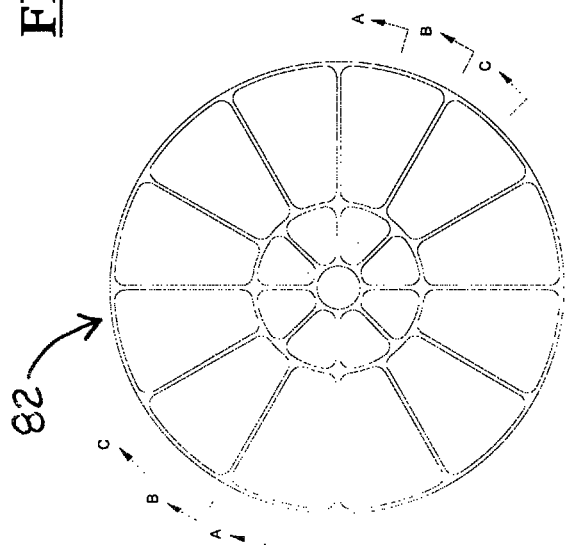

FIGS. 6A-E are diagrams illustrating a main mirror 82 of the optical observation device 22 of the present disclosure. FIG. 6A is a partial cross-sectional top view of main mirror 82 of the optical observation device 22 of the present disclosure. FIG. 6B is a partial cross-sectional view (taken along line A-A of FIG. 6A) of the main mirror 82 of FIG. 6A. FIG. 6C is a partial cross-sectional view (taken along line C-C of FIG. 6A) of the main mirror 82 of FIG. 6A. FIG. 6D is a partial cross-sectional view (taken along line B-B of FIG. 6A) of the main mirror 82 of FIG. 6A. FIG. 6E is a top view of main mirror 82 of the optical observation device 22 of the present disclosure. The optics components (e.g., main mirror 82) of the optical observation device 22 are formed from a metal matrix composite (e.g., aluminum with SiC or $Al_2O_3$ particulate) and can be manufactured using 3D printing or other suitable manufacturing techniques know to the art. Significant improvement of the optical qualities (e.g., reflectivity, frequency response, overall improvement of the signal-to-noise ratio, etc.) of the optical observation device 22 can be obtained by minimizing the effects of interfering radiation. To minimize the effects of interfering radiation, the optics components could be coated with, or otherwise printed with, a metamaterial surface, which is made possible by the extraordinary stiffness and stability of the metal matrix composite employed for the optical surfaces. Metamaterial structures are mathematically defined structures that provide characteristics not found "in nature." The metal matrix composite and metamaterial surface allow the system 10 to utilize large-aperture optics for detecting lower-wavelength spectral bands than were previously accessible.

Figure 7:
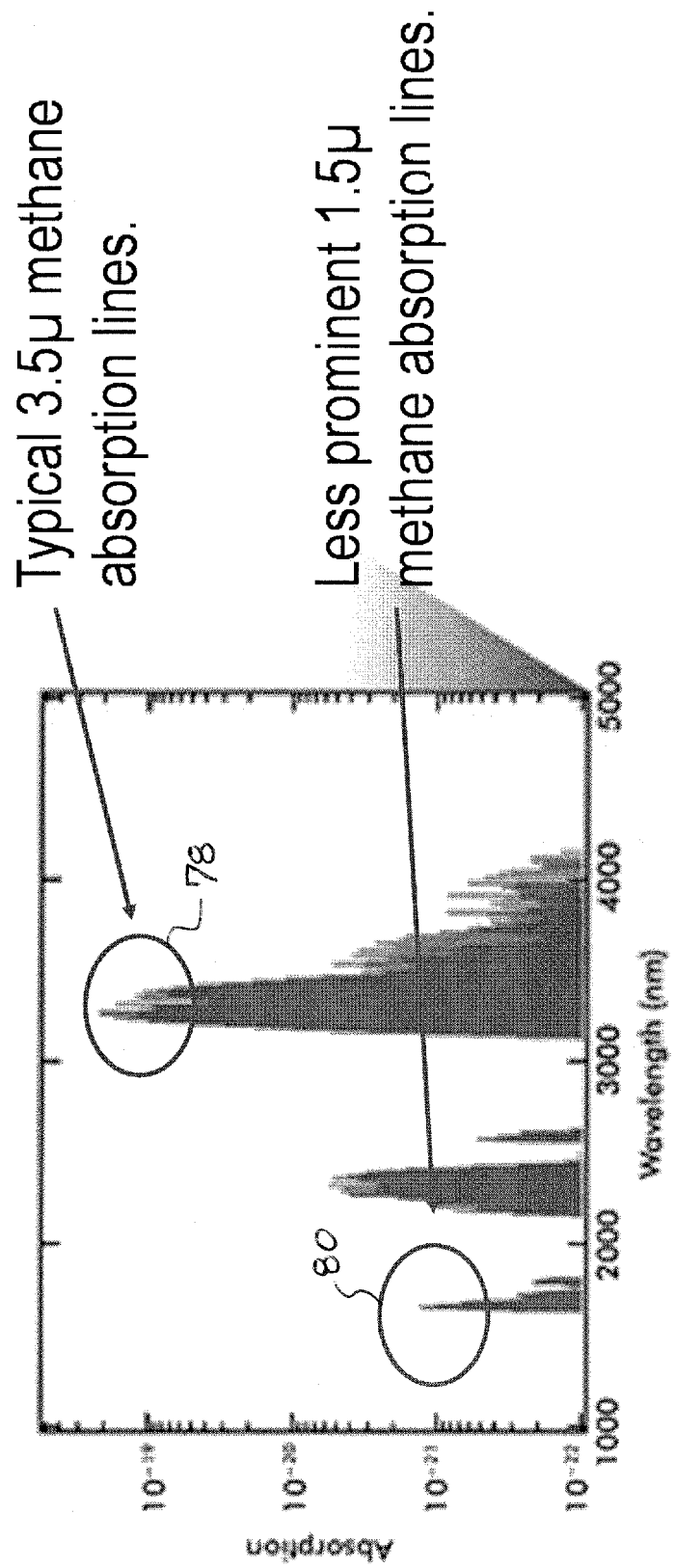
FIG. 7 is a diagram illustrating spectral bands that can be detected by the scanning system of FIG. 5.

FIG. 7 is a diagram illustrating spectral lines, heretofore unusable, which are detected and utilized by the system 10 of the present disclosure for detection of the greenhouse gas, methane. FIG. 7 shows typical 3.5μ methane absorption lines 78 as well as, less prominent, 1.5μ methane absorption lines 80 that are utilized by the system 10.

Figure 9:
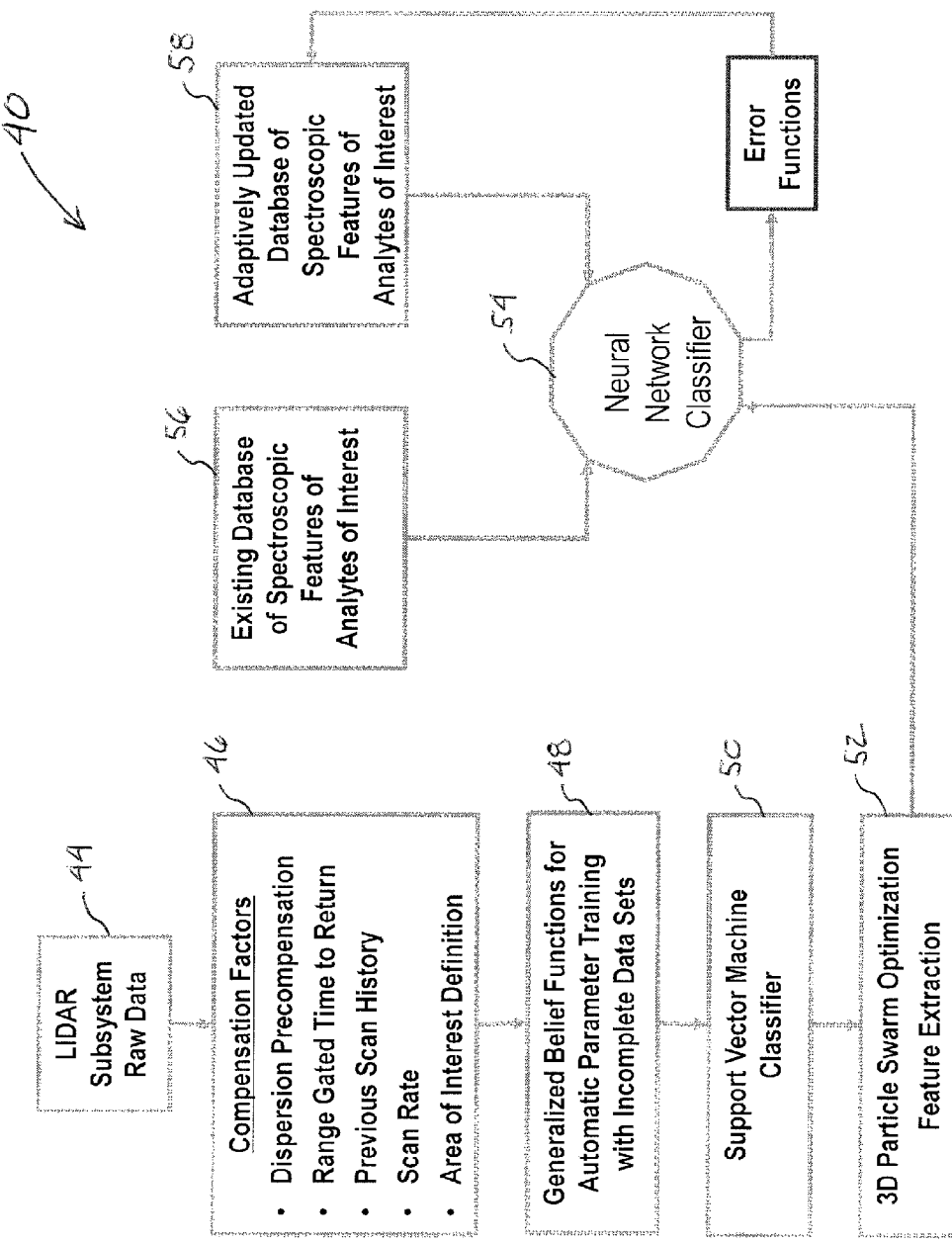
FIG. 9 is a flowchart illustrating processing steps carried out by the signal analysis subsystem of the scanning system of FIG. 5.

FIG. 9 is a flowchart illustrating processing steps of the signal analysis subsystem 40 for the analysis of the raw data captured from the various spectral wavelengths. Typical spectroscopy can employ an average of data responses to fit a "curve" matching a typical spectroscopic response of a perfect analyte. The system 10 of the present disclosure employs the complete data set from a range of frequency subsystems 10a, described in connection with FIG. 8 above. As shown in FIG. 9, the time-sequenced raw datasets undergo a sequence of dimensionality reduction operations by way of a statistical pattern recognition (SPR) approach, merging multiple parameters from the LIDAR system raw data in conjunction with machine learning algorithms. Using the SPR approach, the relevant data can be extracted from a large dataset, while potential missing or corrupted datasets can be "ghosted" on a statistical level by evidential belief methodologies. In step 44, signal analysis subsystem 40 receives LIDAR raw data (e.g., data generated from laser or LED light), as described in connection with FIGS. 5 and 8. In step 46, signal analysis subsystem 40 parameterizes the raw data to affect a large dataset of heterogeneous parameters (e.g., time of flight response to range gating, difference in response between the various wavelengths, precompensation, analyte specific settings, etc.).

Parameterization of the raw data is made possible by the use of a plurality of laser diode driver assemblies 14 which output light at a plurality of discrete wavelengths, for excitation of the target area of interest 12. Unlike a frequency comb, where the position of a frequency, its intensity, and the responses are all subject to variation from environmental parameters and component aging, the utilization of multiple discrete lasers 14 by the system 10 of the present disclosure permits independent calibration of intensity and frequency, thus mitigating environmental interference and aging effects. In step 48, signal analysis subsystem 40 modifies the parameterized data output of step 46 by a set of belief functions derived from experimental analysis of the analytes of interest. The belief functions provide an adaptive means for processing the data from the array of frequency separated lasers 14, the uncertainty of responses due to interferents (e.g., incomplete data sets), and ultimately the "trustworthiness" of the data. The belief functions are continuously modified/updated, building a history of the device, the components, and the installation, which can be used to evaluate the trustworthiness of the final outcome of the dataset. In step 50, signal analysis subsystem 40 reduces the dimensionality of the output of step 48 by a set of classifiers using, for example, a Support Vector Machine (SVM).

In step 52, the SVM output is used as one of the inputs to a three dimensional (3D) Particle Swarm Optimization (PSO) algorithms. Here, the large datasets provided by the foregoing steps are analyzed using image processing software and algorithms, allowing for frameless image capture. Each voxel or 3D image element contains data fields corresponding to the response from a particular laser frequency, the intensity, the time sequence, and a comparison with historical data from a particular point in space. Using this data and the image processing software and algorithms, the signal analysis subsystem 40 can generate "time slice" elements which are similar to the "frames" captured by a standard video camera, while also providing the capability to converge on a small point (in time or space), resulting in seamless variable resolution. Particle swarm optimization (PSO) is employed for the purpose of feature selection (e.g., detection and categorization of "clouds" of detected analytes). The PSO algorithm is based on a repetitive computational architecture, which can be efficiently processed by graphics processing units (GPUs), but can also be run on a general-purpose CPU. The PSO algorithm also stores a history of past iterations to memory, which permits the assessment of anomalies against the current baseline of detection. The 3-D PSO is key to achieving a mass fraction of analyte reading per unit volume. The x-y scanned spectroscopic information is added to the range-gated (z-direction) positional information to provide a time-sliced volumetric distribution of analyte mass, which then can be used to calculate overall flux as well as dispersion and other parameters.

In step 56, signal analysis subsystem 40 transmits data from an existing database of spectroscopic features of analytes of interest to a neural network array. In step 54, signal and analysis subsystem 40 utilizes the adaptive neural network array to perform a determination of concentration and mass per unit volume based on the information received from the theoretical database and an adaptively updated or machine learning enhanced database, discussed hereinbelow.

In step 58, signal analysis subsystem 40 transmits the results of step 54, and error functions, to the adaptive database for a continuous performance enhancement, as well as compensation for equipment aging parameters. Error functions are created by comparing the output of the neural network decision support system with historical or "training" parameters. Errors can occur when the training data does not correctly represent the required analysis function due to external noise or perturbation in the exciting laser pulses due to dust, occlusion, atmospheric perturbations, or in the event that changes in the scene being observed exceed the capability of the instrument to sample. The process then returns to step 54. The neural network classifier provides a confidence level of the concentration or mass fraction of the analyte of interest at each point in the point cloud. From this 3-dimensional, time sequenced set of values, numerous datasets can be created that are tailored for the overall use case of the system 10. For example, the mass fraction of the analyte of interest from all the data points within a specific volume over a defined area (or piece of equipment) of interest 12 may be calculated, to provide a "flux" of material lost or ejected from the area of observation 12. This is critical in providing persistent surveillance of an installation for regulatory requirements. In addition, other operations could superimpose an optical image of the area of interest 12 with the data from the point cloud with a referenced "colorized" scale of confidence (e.g., showing where leakages occurred, their concentration in the absolute sense, and even superimposing a confidence level value). The system 10 could thus detect the flux of the analytes (e.g., methane) on a frame-by-frame basis (e.g., at least 1 second per frame (fine resolution) and/or a video frame rate of at least 30 frames per second (in coarse resolution)) and the system 10 can detect changes in cloud size at a resolution of 1 cubic meter. Accordingly, the minimum detectable mass difference is in the order of grams per second.

The returned raw data will be spread over multiple discrete wavelengths bracketing the analyte(s) of interest. The components of the returned spectrum will be given by scattering and continuum components that have a smooth variation with respect to wavelength. Overall, the intensity (I) of the returned spectrum can be divided into two parts:

$$I = I_0 \exp\left[\sum_i (\beta_i^* + \alpha_i)\sigma_i\right]$$

Where $I_o$ is the intensity of the molecules of interest and $\alpha$ is the continuum component of the spectrum and $\beta^*$ is that which reflects the differential cross-section.

Therefore:

$$\delta_d + \delta_c = \ln\left(\frac{I_{1d}}{I_{2d}}\right) + \ln\left(\frac{I_{1c}}{I_{2c}}\right) =$$
$$\sum_i (\beta_i^* + \alpha_i)(\sigma_{i2} - \sigma_{i1}) = \sum_i \beta_i^*(\sigma_{i2} - \sigma_{i1}) + \sum_i \alpha_i(\sigma_{i2} - \sigma_{i1})$$

Where $\delta_d$ reflects the differential optical depth (DOD). Removing the continuum components and adding in the wavelength dependence produces a matrix equation with which to do the inversion:

$$\delta_d(\lambda) = \sigma_i \beta_i^*(\lambda) \Delta \sigma_i$$

The above depicts a two-frequency (and conversely wavelength) detection approach. However, the system 10 of the present disclosure could include an n-frequency detection approach by which a much higher granularity of detection coupled by a significantly greater bandwidth and signal-to-noise ratio can be effected.

The location of a particular cloud of analytes of interest will be affected via time-of-flight ranging from features of interest in the time domain of the returned signal. The system 10 timestamps every data element. Large datasets having timestamped information provide capabilities such as ad-hoc data analytics and recursive analysis of streams of data, providing event histories for forensic analysis of site planning, remediation results, and meteorological effects on fugitive emissions.

FIGS. 10A-D are diagrams comparing the features of the system 10 of the present disclosure to the current state of the art. FIG. 10A is a diagram illustrating that current state of the art MWIR (mid-wavelength infrared) systems only detect the relative concentration of airborne analytes and are dependent on the background. FIG. 10B is a diagram illustrating that current state of the art CLaDS (Chirped mode Laser Dispersion Spectroscopy), TLDS (Tunable Laser Diode Spectroscopy), and CRDS (Cavity Ring-Down Spectroscopy) systems detect the absolute concentration of airborne analytes and are not background dependent, but only provide a two-dimensional point cloud. FIG. 10C is a diagram illustrating that the system 10 of the present disclosure is able to detect the absolute concentration of airborne analytes, provide a volumetric "cloud of points," and is independent of the background. FIG. 10D is a diagram illustrating that the system 10 of the present disclosure provides a continuous determination of a mass fraction of an analyte of interest independent of background concentration or environmental conditions.

Figure 11:
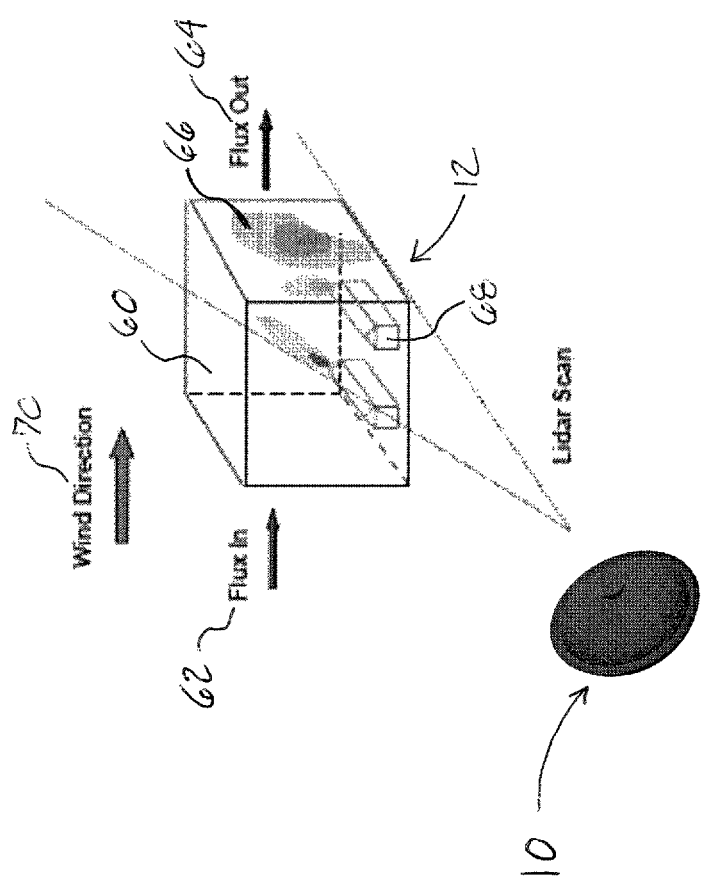
FIG. 11 is a diagram illustrating operation of the scanning system of the present disclosure.

FIG. 11 is a diagram illustrating the operation of the system 10 of the present disclosure in a field environment to detect the concentration of clouds of analytes, their respective positions and concentrations over time, and the resulting changes in mass fraction which may be used to calculate the flux of the effluent to be analyzed, whether it be volatile organic compounds, aerosols, particulates, or even biological material. As illustrated in FIG. 11, the system 10 scans a 3D field 60 ("a 3-D envelope") around and above the area of interest 12. The 3-D envelope 60, in simple terms, is the area in which the airborne materials are detected, the 3-D envelope 60 having a depth, height, and width. The 3-D envelope 60 is a volume that does not need to have (although it could have) hard boundaries (such as, for example, the walls of a room). In other words, the 3-D envelope 60 could be an area within an "imaginary bubble" that surrounds a gas production site, for example. Further, the 3-D envelope 60 could have a variable geometry, permitting fast, high-definition scans of more focused areas of interest 12 (e.g., an area around a valve or pipe fitting that may be leaking gas, as discussed herein in connection with FIG. 12).

The system 10 of the present disclosure permits the scanning of mass fractions of analytes of interest at the boundaries of the 3-D envelope 60 as shown by boundaries 62, 64. The mass fraction of the clouds of analytes 66 changes in time, and the rapid scanning of the system 10 permits the calculation of mass fraction within the 3-D envelope 60 in each "time slice." Knowledge of the boundary conditions of the 3-D envelope 60 and the change in mass fractions per unit time, permits the calculation of the change in mass fraction of the analyte of interest within the 3-D envelope 60 independent of wind velocity 70 as highlighted by the emissions from the simulated structures 68. The resulting change in mass fraction in the scanned 3-D envelope 60 can be assumed to be due to the fugitive emission of materials from the structures 68 and related fixturing, hence the "flux" of the overall emissions.

Figure 12:
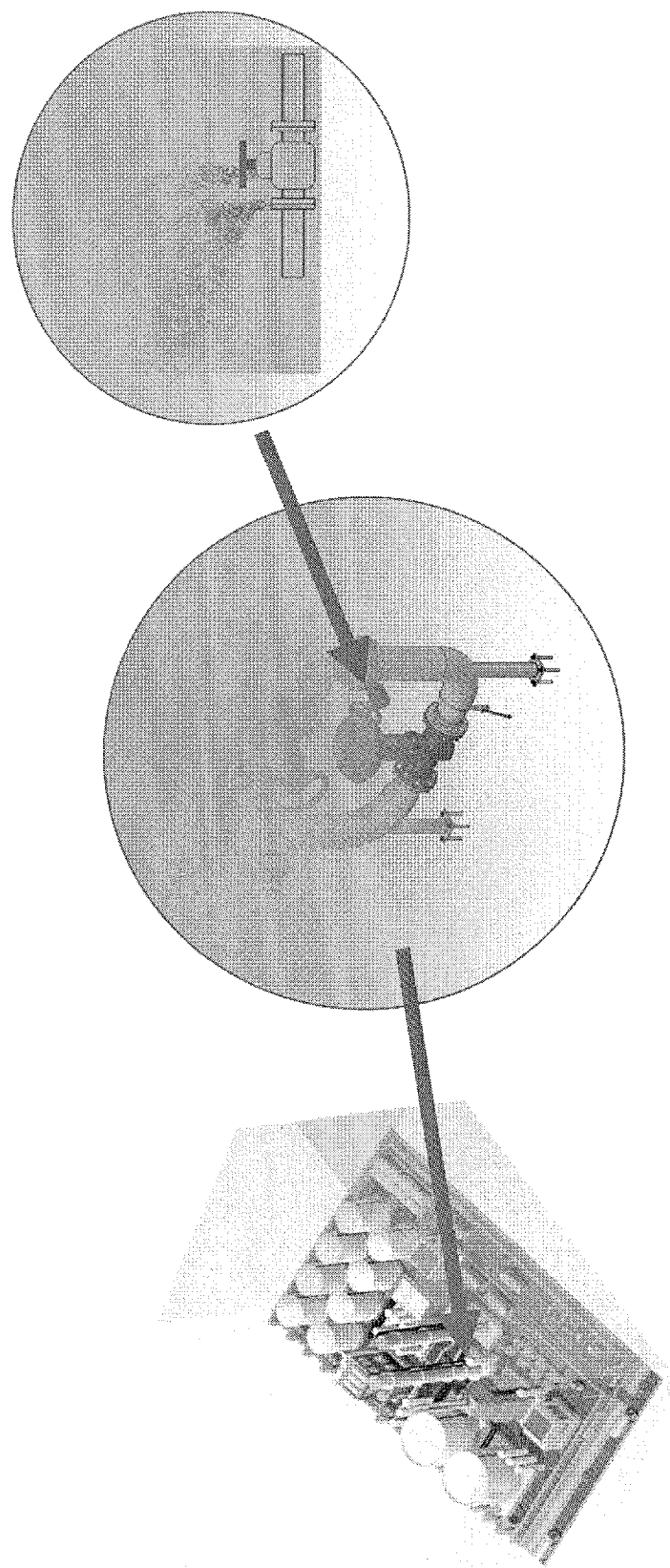
FIG. 12 is a diagram illustrating selective scanning capabilities of the scanning system of the present disclosure.

FIG. 12 is a diagram illustrating the selective scanning capabilities of the system 10. The system 10 detects and tracks a leak using the systems and methods described herein and could further utilize image processing systems (e.g., confocal (co-located) cameras) for mapping concentrations at the area of interest 12. The system 10 could provide a selective resolution depending on the field of use and the resolution desired in the implementation. The system 10 determines the component responsible for the leak and could take remedial action (e.g., transmitting a control signal to valve actuators to stop flow of material to damaged component, notifying maintenance personnel, etc.).

Software programming code which embodies the present disclosure could be stored in permanent storage. In a client/server environment, such software programming code could be stored with storage associated with a server. The software programming code can be stored on any of a variety of known computer-readable media for use with a data processing system, such as a diskette, hard drive, CD-ROM, etc. The code could be distributed on such media, or may be distributed to users from the memory or storage of one computer system over a network of some type to other computer systems for use by users of such other systems. The system 10 could also utilize cloud-based computing for centralized operations centers or for providing selected datasets to different groups of users (e.g., regulatory, well owners, end customers, etc.).

These program instructions can be provided to a processor to produce a machine, such that the instructions that execute on the processor create means for implementing the functions specified in the illustrations. The computer program instructions could be executed by a processor, or a series of parallel processors, to cause a series of operational steps to be performed by the processor to produce a computer-implemented process such that the instructions that execute on the processor provide steps for implementing the functions specified in the illustrations. Accordingly, the figures support combinations of means for performing the specified functions, combinations of steps for performing the specified functions, and program instruction means for performing the specified functions.

Having thus described the disclosure in detail, it is to be understood that the foregoing description is not intended to limit the spirit or scope thereof. What is desired to be protected is set forth in the following claims.

What is claimed is:

1. A system for detecting airborne materials in a 3-dimensional envelope, comprising:
   a laser diode driver assembly;
   a modulator assembly operatively coupled to said laser diode driver assembly for conditioning and modulating light emitted by said laser diode driver assembly;
   a scanning array for directing the conditioned and modulated light to the 3-dimensional envelope;
   an optical observation device for collecting backscatter radiation signals from the 3-dimensional envelope;
   a detection array for receiving the collected backscatter radiation signals; and
   a signal analysis subsystem for analyzing the backscatter radiation signals using a machine learning algorithm to identify at least one feature of an analyte in the 3-dimensional envelope.

2. The system of claim 1, wherein the detection array heterodynes the collected backscatter radiation signals with a reference signal, the reference signal generated by an optical splitter in communication with the laser diode driver assembly.

3. The system of claim 1, wherein the laser diode driver assembly emits light at one or more wavelengths corresponding to airborne materials to be detected.

4. The system of claim 1, further comprising one or more discrete wavelength subsystems, each subsystem being tuned to wavelengths corresponding to a specific analyte of interest.

5. The system of claim 3, wherein the laser diode driver assembly emits light at the $1.5\mu$-$1.65\mu$ wavelengths.

6. The system of claim 4, wherein the one or more discrete wavelength subsystems includes a tunable laser, an optical splitter, a range gated pulse shaper, a circulator, a combiner, and an avalanche photo diode having a frequency response matching the tunable laser.

7. The system of claim 6, further comprising a control and communication subsystem providing synchronization between remote wavelength subsystems.

8. A method for detecting airborne materials in a 3-dimensional envelope, comprising the steps of:
emitting light from a laser diode driver assembly at one or more wavelengths corresponding to airborne materials to be detected;
conditioning and modulating the light emitted by said laser diode driver assembly;
directing the conditioned and modulated light to the 3-dimensional envelope;
collecting backscatter radiation signals from the 3-dimensional envelope using an optical observation device;
receiving the collected backscatter radiation signals at a detection array; and
analyzing the backscatter radiation signals using a machine learning algorithm to identify at least one feature of an analyte in the 3-dimensional envelope.

9. The method of claim 8, further including the step of receiving raw data from the detection array and parameterizing the raw data to produce a dataset of heterogeneous parameters.

10. The method of claim 9, further including the step of modifying the dataset by a set of belief functions corresponding to the airborne materials to be detected.

11. The method of claim 10, further including the step of reducing dimensionality of the modified dataset using a support vector machine.

12. The method of claim 11, further including the step of performing particle swarm optimization on an output of the support vector machine.

13. The method of claim 12, further including the step of utilizing an adaptive neural network to perform a determination of concentration and mass using data from a theoretical database, an adaptively updated database, and the particle swarm optimized output of the support vector machine.

14. The method of claim 13, further including the step of applying error functions to an output of the adaptive neural network and transmitting resulting data to the adaptively updated database.

15. The method of claim 14, further including the step of returning to the step of utilizing an adaptive neural network to perform a determination of concentration and mass using data from the theoretical database, the adaptively updated database, and the particle swarm optimized output of the support vector machine.

16. A system for detecting airborne materials in a 3-dimensional envelope, comprising:
a light-emitting diode driver assembly;
a modulator assembly operatively coupled to said light-emitting diode driver assembly for conditioning and modulating light emitted by said light-emitting diode driver assembly;
a scanning array for directing the conditioned and modulated light to the 3-dimensional envelope;
an optical observation device for collecting backscatter radiation signals from the 3-dimensional envelope;
a detection array for receiving the collected backscatter radiation signals; and
a signal analysis subsystem for analyzing the backscatter radiation signals using a machine learning algorithm to identify at least one feature of an analyte in the 3-dimensional envelope.

17. The system of claim 16, wherein the detection array heterodynes the collected backscatter radiation signals with a reference signal, the reference signal generated by an optical splitter in communication with the light-emitting diode driver assembly.

18. The system of claim 16, wherein the light-emitting diode driver assembly emits light at one or more wavelengths corresponding to airborne materials to be detected.

19. The system of claim 16, further comprising one or more discrete wavelength subsystems, each subsystem being tuned to wavelengths corresponding to a specific analyte of interest.

20. The system of claim 18, wherein the light-emitting diode driver assembly emits light at the $1.5\mu$-$1.65\mu$ wavelengths.

21. The system of claim 19, wherein the one or more discrete wavelength subsystems includes a light-emitting diode, an optical splitter, a range gated pulse shaper, a circulator, a combiner, and an avalanche photo diode having a frequency response matching the light-emitting diode.

22. The system of claim 21, further comprising a control and communication subsystem providing synchronization between remote wavelength subsystems.

23. A method for detecting airborne materials in a 3-dimensional envelope, comprising the steps of:
emitting light from a light-emitting diode driver assembly at one or more wavelengths corresponding to airborne materials to be detected;
conditioning and modulating the light emitted by said light-emitting diode driver assembly;
directing the conditioned and modulated light to the 3-dimensional envelope;
collecting backscatter radiation signals from the 3-dimensional envelope using an optical observation device;
receiving the collected backscatter radiation signals at a detection array; and
analyzing the backscatter radiation signals using a machine learning algorithm to identify at least one feature of an analyte in the 3-dimensional envelope.

24. The method of claim 23, further including the step of receiving raw data from the detection array and parameterizing the raw data to produce a dataset of heterogeneous parameters.

25. The method of claim 24, further including the step of modifying the dataset by a set of belief functions corresponding to the airborne materials to be detected.

26. The method of claim 25, further including the step of reducing dimensionality of the modified dataset using a support vector machine.

27. The method of claim 26, further including the step of performing particle swarm optimization on an output of the support vector machine.

28. The method of claim 27, further including the step of utilizing an adaptive neural network to perform a determination of concentration and mass using data from a theoretical database, an adaptively updated database, and the particle swarm optimized output of the support vector machine.

29. The method of claim 28, further including the step of applying error functions to an output of the adaptive neural network and transmitting resulting data to the adaptively updated database.

30. The method of claim 29, further including the step of returning to the step of utilizing an adaptive neural network to perform a determination of concentration and mass using data from the theoretical database, the adaptively updated database, and the particle swarm optimized output of the support vector machine.

\* \* \* \* \*